United States Patent
Eby et al.

(10) Patent No.: US 12,296,181 B2
(45) Date of Patent: May 13, 2025

(54) BIOSTIMULATOR TRANSPORT SYSTEM HAVING SWAGED TORQUE SHAFT

(71) Applicant: Pacesetter, Inc., Sylmar, CA (US)

(72) Inventors: Thomas B. Eby, Mountain View, CA (US); Joe Callol, San Mateo, CA (US); Arundhati Kabe, Cupertino, CA (US); Daniel Coyle, Saint Louis Park, MN (US)

(73) Assignee: PACESETTER, INC., Sylmar, CA (US)

( * ) Notice: Subject to any disclaimer, the term of this patent is extended or adjusted under 35 U.S.C. 154(b) by 497 days.

(21) Appl. No.: 16/859,706

(22) Filed: Apr. 27, 2020

(65) Prior Publication Data

US 2021/0138252 A1    May 13, 2021

Related U.S. Application Data

(60) Provisional application No. 62/933,084, filed on Nov. 8, 2019.

(51) Int. Cl.
*A61M 25/01* (2006.01)
*A61N 1/05* (2006.01)
(Continued)

(52) U.S. Cl.
CPC ....... *A61N 1/3756* (2013.01); *A61M 25/0113* (2013.01); *A61N 1/0573* (2013.01);
(Continued)

(58) Field of Classification Search
CPC ............. A61B 17/32; A61B 17/32002; A61B 2017/320024; A61B 2017/320032; A61B 17/1631; A61M 25/0113; A61M 25/0053; A61M 25/0054; A61M 25/0138; A61M 25/0141; A61M 25/0144; A61M 25/09; A61M 25/09016; A61M 25/09025;
(Continued)

(56) References Cited

U.S. PATENT DOCUMENTS

| | | | | |
|---|---|---|---|---|
| 1,649,310 A | * | 11/1927 | Joline | F16C 1/08 428/592 |
| 1,952,301 A | * | 3/1934 | Webb | F16C 1/02 57/213 |
| 5,154,705 A | * | 10/1992 | Fleischhacker | A61B 17/3207 600/585 |

(Continued)

*Primary Examiner* — Diane D Yabut
*Assistant Examiner* — Christian D Knauss
(74) *Attorney, Agent, or Firm* — WOMBLE BOND DICKINSON (US) LLP (57) ABSTRACT

A biostimulator transport system, such as a biostimulator delivery system, having a swaged torque shaft, is described. The torque shaft includes an outer cable coaxially arranged with an inner coil. The inner coil has a single wire coil extending around a central axis in a first helical direction, and the outer cable has several outer strands that extend around the central axis in a second helical direction that is different than the first helical direction. The outer cable can be swaged to form a close fit to the inner coil. The close fit of the swaged coaxial torque shaft structure can track to a target site through tortuous vessels and efficiently transfer torque from a handle to a docking cap of the biostimulator transport system to drive a biostimulator into the target site. Other embodiments are also described and claimed.

26 Claims, 7 Drawing Sheets

(51) Int. Cl.
*A61N 1/375* (2006.01)
*F16C 1/02* (2006.01)

(52) U.S. Cl.
CPC ............ *A61N 1/37512* (2017.08); *F16C 1/02* (2013.01); *A61N 2001/0578* (2013.01); *A61N 2001/058* (2013.01)

(58) Field of Classification Search
CPC ............ A61M 25/09033; A61M 2025/09058; A61M 2025/09066; A61M 2025/09075; A61M 2025/09083; A61M 2025/09091; A61M 2025/09108; A61M 2025/0915; A61M 2025/09191
See application file for complete search history.

(56) References Cited

U.S. PATENT DOCUMENTS

| | | | |
|---|---|---|---|
| 5,816,923 A * | 10/1998 | Milo | A61B 17/320758 464/902 |
| 6,267,679 B1 * | 7/2001 | Romano | F16C 1/02 175/320 |
| 7,985,214 B2 | 6/2011 | Garabedian et al. | |
| 8,377,035 B2 | 2/2013 | Zhou et al. | |
| 2002/0151823 A1 * | 10/2002 | Miyata | A61M 25/09 600/585 |
| 2004/0243108 A1 * | 12/2004 | Suzuki | F16C 1/02 606/1 |
| 2016/0066947 A1 * | 3/2016 | Mitelberg | A61B 17/3201 606/170 |
| 2018/0104440 A1 * | 4/2018 | Hanaoka | A61M 25/0068 |
| 2018/0104449 A1 | 4/2018 | Arnar et al. | |
| 2018/0104450 A1 | 4/2018 | Rickheim et al. | |
| 2018/0104451 A1 | 4/2018 | Kerns et al. | |
| 2018/0104452 A1 | 4/2018 | Goodman et al. | |
| 2018/0280703 A1 | 10/2018 | Hillukka et al. | |
| 2018/0303513 A1 | 10/2018 | Kerns et al. | |
| 2018/0303514 A1 | 10/2018 | Coyle et al. | |
| 2018/0339139 A1 * | 11/2018 | Boucher | A61M 25/09016 |

* cited by examiner

BIOSTIMULATOR TRANSPORT SYSTEM HAVING SWAGED TORQUE SHAFT

This application claims the benefit of priority of U.S. Provisional Patent Application No. 62/933,084, filed Nov. 8, 2019, entitled "Biostimulator Transport System Having Swaged Torque Shaft," and that patent application is incorporated herein by reference in its entirety to provide continuity of disclosure.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Field

The present disclosure relates to biostimulators and related delivery and retrieval systems and methods. More specifically, the present disclosure relates to transport systems for delivery or retrieval of leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The generator usually connects to a proximal end of one or more implanted leads, the distal end of which contains one or more electrodes for positioning adjacent to the inside or outside wall of a cardiac chamber. Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

Leadless cardiac pacemakers incorporate electronic circuitry at the pacing site and eliminate leads, and thus, avoid the above-mentioned shortcomings of conventional cardiac pacing systems. Leadless cardiac pacemakers can be anchored at the pacing site by an anchor. During delivery or retrieval of a leadless cardiac pacemaker, a transport system can apply torque to the leadless cardiac pacemaker via a docking cap to screw the anchor into, or out of, the target tissue.

SUMMARY

Existing transport systems used for delivery or retrieval of leadless cardiac pacemakers may have a torque transmission component to apply torque to a leadless cardiac pacemaker. For example, the torque transmission component may be an elongated cable that connects a docking cap to a handle of the transport system. The handle can be rotated to transmit torque through the cable to rotate the leadless cardiac pacemaker when it is attached to the docking cap. The torque transmission component may transmit torque, however, an efficiency of that torque transfer may be less than optimal. For example, the torque transmission component may be rotationally soft such that, as an input rotation is applied at an input end, energy is stored in the elongated cable without resulting in an output rotation at the docking cap. This phenomenon is referred to as "wind up." Wind up can occur until an angular (or energy) threshold is met, at which point an output end of the cable can quickly rotate or whip to a new angular position that may or may not match an angular position of an input end of the cable. This phenomenon is referred to as "unloading" or "whip." In other words, the output twist may lag the input twist in existing torque transmission components, which can result in poor torque transmission and a lack of correspondence between the input end and the output end of the torque transmission component. In short, correspondence between the input end and the output end is ideally a direct correlation (1:1 ratio) to ensure that rotation at the handle of the transport system matches rotation of the biostimulator within a patient, and this ideal is not met by existing transport systems.

A biostimulator transport system having a swaged torque shaft that promotes a direct correlation between an input rotation at a handle and an output rotation at a docking cap, is provided. The biostimulator transport system can be a catheter-based system for delivering or retrieving a leadless pacemaker. In an embodiment, the biostimulator transport system includes the handle coupled to a proximal end of the torque shaft, and the docking cap coupled to a distal end of the torque shaft. An intermediate component, such as a hypotube, can connect the proximal end of the torque shaft to the handle. The handle can have one or more portions, e.g., a proximal handle portion and a distal handle portion, and at least one of the handle portions can be twisted to impart the input rotation to the torque shaft. For example, the proximal handle portion can be rotated relative to the distal handle portion to twist the hypotube and transmit torque to and through the torque shaft.

The torque shaft can have a swaged, dual-layer, coaxial construction. More particularly, an outer cable having several strands can be coaxially arranged about an inner coil having a wire coil. The outer strands and the wire coil can extend helically around a central axis. For example, the outer strands can spiral about the central axis in a first helical direction, e.g., right handed rotation, and the wire coil can spiral about the central axis in a second helical direction, e.g., left handed rotation.

The outer cable can be swaged over at least a portion of a length of the torque shaft. For example, the outer cable can be swaged and then loaded onto the inner coil, or the outer cable can be swaged directly onto the inner coil. In either case, the outer cable can be swaged over a portion of, or an entirety, of a coil length of the inner coil. The swaged outer strands can form a friction fit or a slip fit with the wire coil, and thus, torque transmission through the torque shaft can be improved. More particularly, when torque is applied to a proximal end of the torque shaft, one layer of the torque shaft can limit expansion and or contraction of the other layer, and thus, energy storage within the layers can be mitigated. As a result, the torque shaft experiences less wind up and can achieve direct correlation between an input torsional angle of the input torque at the proximal shaft end and an output torsional angle of the output torque at the distal shaft end. The swaged torque shaft can reduce wind up even under objectively challenging scenarios. For example, in one use case, the torque shaft can experience multiple loading conditions at once, e.g., may transmit torque while under a varying compressive load. By way of example and not limitation, the torque shaft can transmit 100 oz-in while under a 5 lbf compressive load. Even under such conditions, the swaged torque shaft can experience reduced wind up and can achieve direct correlation between the input torsional angle and the output torsional angle.

A method of manufacturing the torque shaft is also described. The method includes loading the outer cable over the inner coil. The outer cable can be a in a pre-swaged state such that the outer strands are undeformed, e.g., round wires, or in a post-swaged state such that the outer strands are deformed, e.g., flattened wires. Accordingly, the pre-swaged outer cable can be swaged directly onto the inner coil to form a friction fit, or the post-swaged outer cable can be loaded over the inner coil to form a slip fit. The layers can be attached to each other at the ends of the tubular layers to form the torque shaft. The swaged torque shaft can be connected to the hypotube and/or the docking cap to form the torque shaft assembly. The torque shaft assembly can then be incorporated as a subcomponent of the biostimulator transport system.

In an embodiment, an outer sleeve is used to constrain the inner coil and the outer cable in a mating relationship, in addition to or instead swaging the outer cable. For example, the outer sleeve can be a thin-walled tubular component that surrounds and contains the inner coil and the outer cable. The outer sleeve can have an inner diameter that matches, e.g., is equal to, an outer diameter of the outer cable. For example, the outer sleeve can form a slip, friction, or press fit with the outer sleeve. Accordingly, expansion of the outer cable due to twisting of the torque shaft can be resisted by the hoop strength of the outer sleeve to maintain the inner coil and the outer cable in contact with each other.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Embodiments describe a biostimulator transport system, such as a biostimulator delivery system, having a swaged torque shaft. As described below, the biostimulator transport system can be used to deliver a biostimulator into a heart of a patient to pace cardiac tissue. The biostimulator may, however, be used in other applications, such as deep brain stimulation. Thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a central axis of a torque shaft assembly. Similarly, "proximal" may indicate a second direction opposite to the first direction. Such terms are provided to establish relative frames of reference, however, and are not intended to limit the use or orientation of a biostimulator transport system to a specific configuration described in the various embodiments below.

In an aspect, a torque shaft having coaxially arranged and swaged inner and outer layers is provided to improve torque transmission. The inner layer may be an inner coil including a single wire coil wound about a central axis, e.g., as a stacked coil tube. The outer layer may be an outer cable including several outer strands wound about the inner coil and the central axis. The inner layer and the outer layer can be wound about the central axis in opposite directions, and furthermore, one or more of the layers can be swaged to form one or more of a friction fit or a slip fit between the outer strands and the wire coil. Accordingly, the inner coil and the outer cable can cooperate to reduce wind up and enhance torque transmission. More particularly, as torque is applied to an input end of the torque shaft, the inner and outer layers can cinch against each other to limit an amount of torque-loading in the torque shaft. By limiting torque-loading in the torque shaft, the swaged dual-layer torque shaft can reduce a likelihood of torque "wind up" that can lead to "unloading" and over-rotation of a biostimulator. More particularly, the swaged, coaxial construction of the torque shaft can improve torque transmission to provide a direct correlation between rotations at a handle and rotations at an output end of the torque shaft and/or a docking cap of a biostimulator transport system. As described below, the swaged, coaxial construction also provides adequate column strength and axial rigidity to engage tissue while still being flexible enough in bending to prevent tissue trauma during delivery of the biostimulator to a target site.

Figure 1:
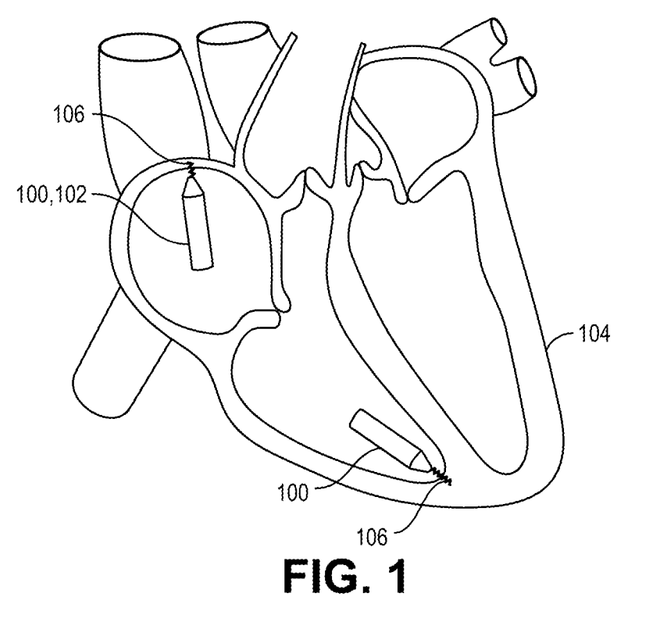
FIG. 1 is a diagrammatic medial-lateral cross section of a patient heart illustrating an example implantation of biostimulators in the patient heart, in accordance with an embodiment.

Referring to FIG. 1, a diagrammatic medial-lateral cross section of a patient heart illustrating an example implantation of biostimulator in the patient heart is shown in accordance with an embodiment. A cardiac pacing system includes one or more biostimulator 100. The biostimulator(s) 100 can be implanted at respective target sites in a patient heart 104. The biostimulator(s) 100 can be leadless, and thus, may be leadless cardiac pacemakers 102. Each biostimulator 100 can be placed in a cardiac chamber, such as a right atrium and/or right ventricle of the patient heart 104, or attached to an inside or outside of the cardiac chamber. Attachment of the biostimulator 100 to the target tissue can be accomplished via one or more fixation elements 106, such as helical anchors. In a particular embodiment, the leadless pacemaker can use two or more electrodes located on or within a housing of the leadless pacemaker for pacing the cardiac chamber upon receiving a triggering signal from internal circuitry and/or from at least one other device within the body.

Figure 2A:
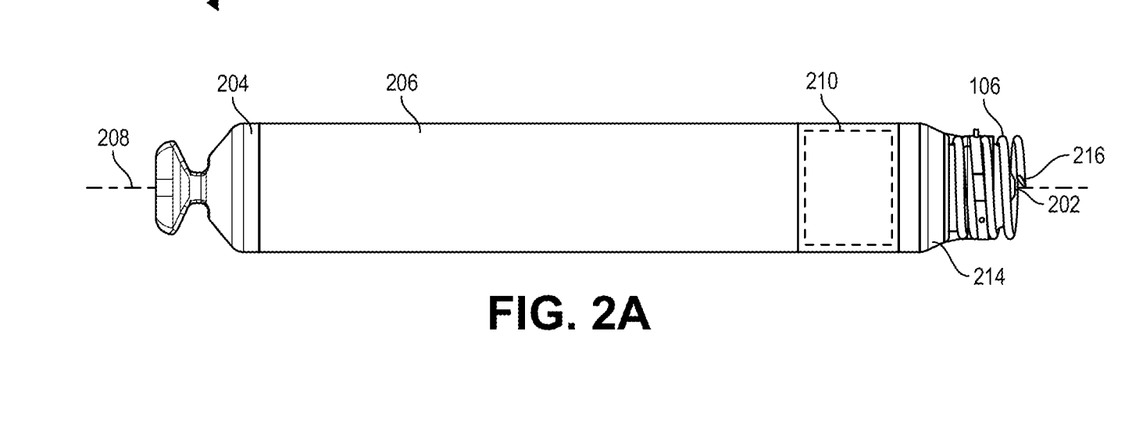
FIGS. 2A-2B are, respectively, side and end views of a biostimulator, in accordance with an embodiment.

Referring to FIG. 2A, a side view of a biostimulator is shown in accordance with an embodiment. The biostimulator 100 can be a leadless cardiac pacemaker 102 that can perform cardiac pacing and that has many of the advantages of conventional cardiac pacemakers while extending performance, functionality, and operating characteristics. The biostimulator 100 can have two or more electrodes, e.g., a distal electrode 202 and a proximal electrode 204, located within, on, or near a housing 206 of the biostimulator 100. In an embodiment, the fixation element 106 forms a portion of the distal electrode 202. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 206 has a longitudinal axis 208, and the distal electrode 202 can be a distal pacing electrode mounted on the housing 206 along the longitudinal axis 208. The housing 206 can contain a primary battery to provide power for pacing, sensing, and communication, which may include, for example, bidirectional communication. The housing 206 can optionally contain an electronics compartment 210 to hold circuitry adapted for different functionality. For example, the electronics compartment 210 can contain circuits for sensing cardiac activity from the electrodes, circuits for receiving information from at least one other device via the electrodes, circuits for generating pacing pulses for delivery via the electrodes, or other circuitry. The electronics compartment 210 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site by one or more actively engaging mechanisms or fixation mechanisms, such as a screw or helical member that screws into the myocardium. In an embodiment, the biostimulator 100 includes the fixation element 106 coupled to the housing 206. The fixation element 106 can be a helical element to screw into target tissue. More particularly, the fixation element 106 can extend helically from a flange 214 of the biostimulator 100, which is mounted on the housing 206, to a distal tip at a helix distal end 216.

Figure 2B:
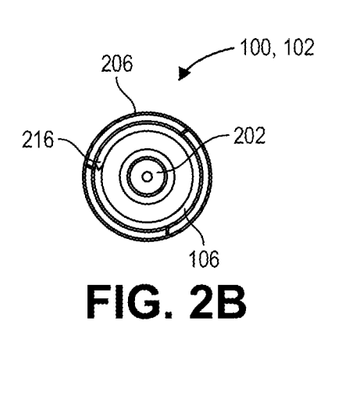

Referring to FIG. 2B, an end view of a biostimulator is shown in accordance with an embodiment. The helix distal end 216 can be located distal to the distal electrode 202 (a centrally located electrode). Accordingly, when the biostimulator 100 contacts the target tissue, the distal tip can pierce the tissue and the housing 206 can be rotated to screw the fixation element 106 into the target tissue to pull the distal electrode 202 into contact with the tissue. By contrast, the housing 206 can be rotated to unscrew the fixation element 106 from the target tissue to retrieve the biostimulator 100.

Leadless pacemakers or other leadless biostimulators 100 can be delivered to and retrieved from a patient using a transport system, as described below. In some implementations, the transport system is a delivery system for delivering the leadless pacemaker to the target tissue. In some implementations, the transport system is a retrieval system for retrieving the leadless pacemaker from the target tissue. Such delivery systems and retrieval systems can incorporate common components, such as a torque shaft or torque shaft assembly as described below.

Figure 3:
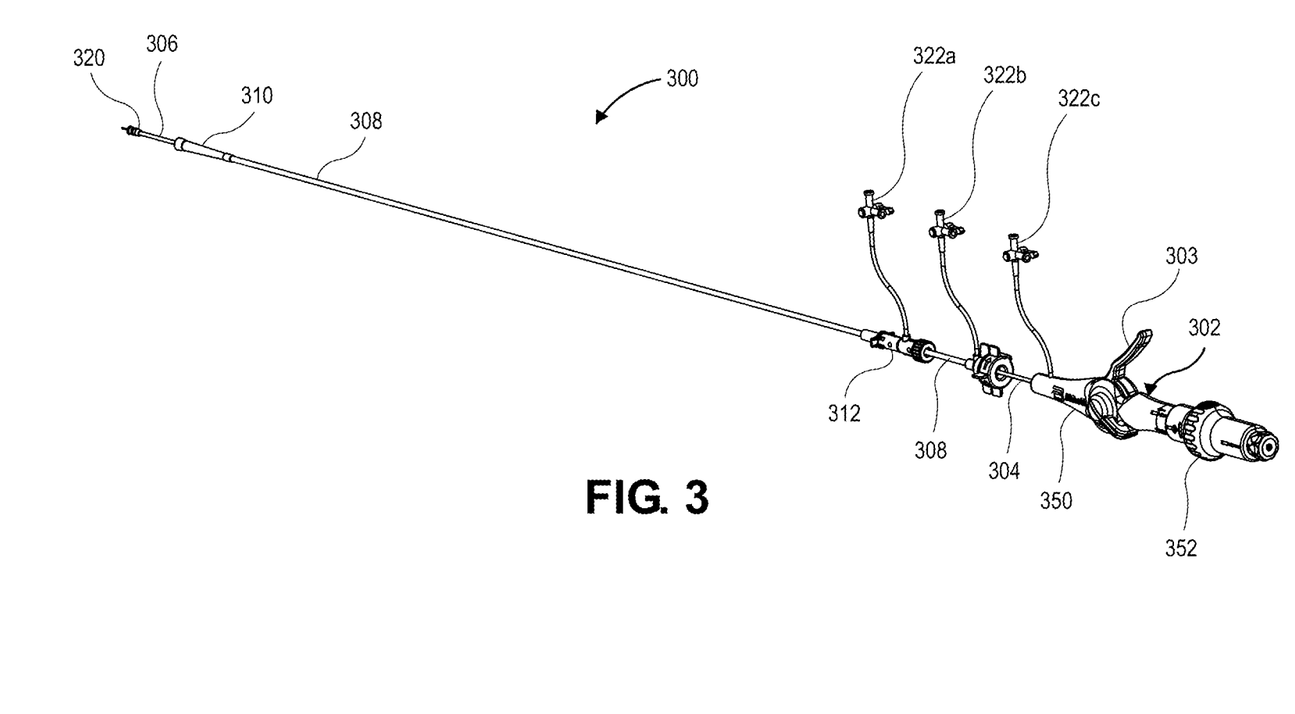
FIG. 3 is a perspective view of a biostimulator transport system, in accordance with an embodiment.

Referring to FIG. 3, a perspective view of a biostimulator transport system is shown in accordance with an embodiment. A biostimulator transport system 300 may be used for delivery and/or retrieval of the biostimulator 100, e.g., a leadless pacemaker, into or from a patient. For example, the biostimulator transport system can be a biostimulator delivery system used for delivery of the biostimulator 100 into a patient. Alternatively, the biostimulator transport system can be a biostimulator retrieval system. The transport system is primarily referred to as being a delivery system for brevity below, however, such reference is non-limiting.

The biostimulator transport system 300 can include a handle 302, and an elongated catheter 304 extending distally from the handle 302 to a distal catheter end 306. The handle 302 can include several portions and features that allow a user to provide inputs at a proximal end of the system that translate to outputs at the distal end of the system. For example, the elongated catheter 304 can be a deflectable catheter, and an operator can use the handle 302 to steer the distal catheter end 306 in the patient. In an embodiment, the handle 302 includes a deflection lever 303 that can be used to deflect the distal catheter end 306. By pivoting the deflection lever 303 toward a distal handle portion 350 of the handle 302, the operator can cause a pull ring assembly (FIG. 5) to apply off-axis compression to the elongated catheter 304, resulting in lateral deflection of the distal catheter end 306. The handle 302 can be used to apply a torque to a docking cap 320 at the distal end of the system. In an embodiment, the handle 302 includes proximal handle portion 352. The proximal handle portion 352 can be rotationally and/or longitudinally moveable relative to the distal handle portion 350. For example, the distal handle portion 350 can be coupled to the elongated catheter 304 and the proximal handle portion 352 can be coupled to a hypotube (FIG. 5), and an operator can rotate the proximal handle portion 352 relative to the distal handle portion 350 to cause the docking cap 320, which is rotationally linked to the proximal handle portion 352, to rotate relative to the elongated catheter 304, which is rotationally linked to the distal handle portion 350. More information about the handle 302 and the handle functionality is described in the publications and patent applications that are incorporated by reference below.

In an embodiment, the biostimulator transport system 300 includes a protective sheath 308 mounted on the elongated catheter 304. The protective sheath 308 can be slidably disposed on the elongated catheter 304. The protective sheath 308 can include an atraumatic end 310, e.g., a soft, funnel-shaped distal portion, that can slide distally over the distal catheter end 306 of the elongated catheter 304 and/or the biostimulator 100 (not shown). The atraumatic end 310 can have an outer dimension, which may be larger than a proximal portion of the protective sheath 308. For example, the atraumatic end 310 may flare in a distal direction to a funnel opening that can advance over a docking cap 320 of the biostimulator transport system 300. An outer dimension of the atraumatic end 310 can be larger than a region of the protective sheath 308 supporting a valve bypass tool 312.

The valve bypass tool 312 can be slidably disposed on the protective sheath 308 such that a distal portion of the valve bypass tool 312 can slide distally over the distal catheter end 306 of the elongated catheter 304 and/or the atraumatic end 310 of the protective sheath 308. More particularly, the valve bypass tool 312 can be inserted into an access introducer to gain access to the patient vasculature, and after access is established, the distal portion of the protective sheath 308 and/or the distal end of the elongated catheter 304 can be advanced through the valve bypass tool 312 into the patient.

The valve bypass tool 312, the protective sheath 308, and the elongated catheter 304 can have respective flush ports 322a, 322b, and 322c extending respectively therefrom. Each of the longitudinal bodies are displaceable proximal-distal relative to each other, and thus, the flush ports can be used to introduce and/or flush saline or other fluids between the longitudinal bodies or through the respective components in different relative positions.

Figure 4:
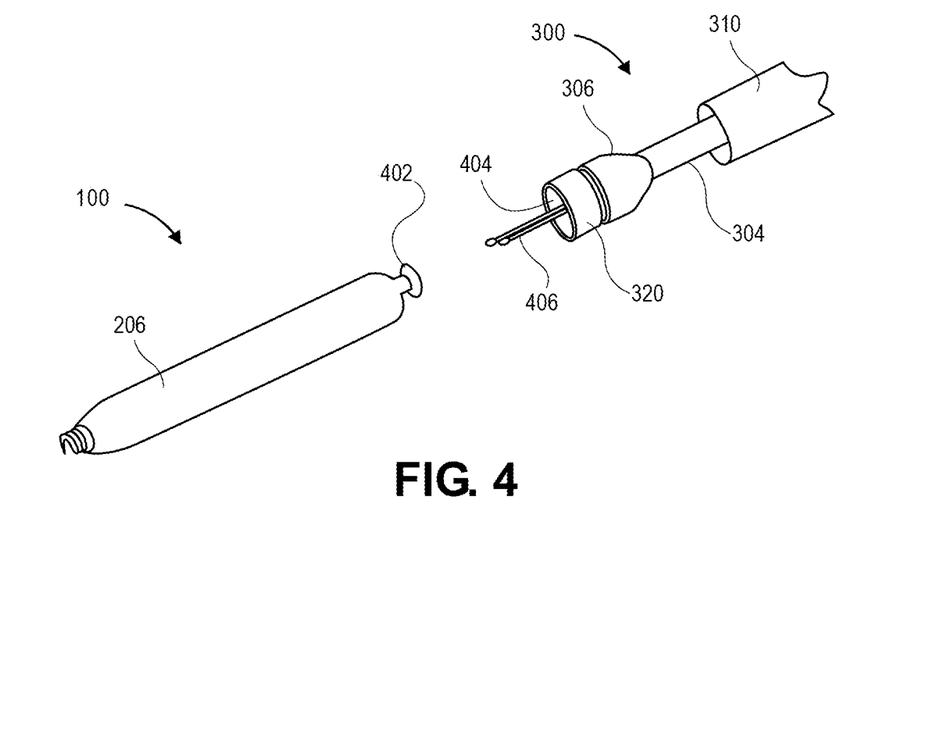
FIG. 4 is a distal perspective view of a biostimulator transport system having a docking cap to receive a biostimulator, in accordance with an embodiment.

Referring to FIG. 4, a distal perspective view of a biostimulator transport system having a docking cap to receive a biostimulator is shown in accordance with an embodiment. The distal catheter end 306 of the elongated catheter 304 may be selectively connectable to the biostimulator 100. More particularly, the biostimulator 100 can be mounted on the distal catheter end 306 of the elongated catheter 304. In an embodiment, the biostimulator 100 includes an attachment feature 402. The attachment feature 402 can be, for example, a protuberance extending proximally from the housing 206. In an embodiment, the attachment feature 402 includes a channel (not shown) shaped and sized to receive one or more tethers 406. The tethers 406 can comprise wires, shafts, tubes, cords, ropes, strings, or other similar structures that can extend throughout the catheter shaft 304. For example, the tethers 406 can extend through a central lumen of a torque shaft assembly. In an embodiment, the tethers 406 include one or more snare wires having loops that can wrap or grasp around the attachment feature 402. In some embodiments, the tethers comprise a shape memory material, such as nickel-titanium. In other embodiments, the tethers comprise stainless steel wires or braids. The tethers 406 can be inserted into and locked within the attachment feature 402 to connect the biostimulator 100 to the biostimulator transport system 300. In other embodiments, the tethers 406 can be formed from wire or mechanical linkages created by processes such as machining, molding (metallic or polymer materials), or other fabrication processes.

The attachment feature 402 can have a shape and size that fits within a docking cavity 404 of the docking cap 320. When the tethers 406 are locked within the attachment feature 402, the tethers 406 can be retracted to pull the biostimulator 100 toward the docking cap 320. As the biostimulator 100 moves toward the docking cap 320, the attachment feature 402 can insert into the docking cavity 404. Accordingly, the docking cavity 404 can receive the attachment feature 402 to dock the biostimulator 100 to the biostimulator transport system 300 for delivery or retrieval from the patient.

The biostimulator 100 can be protected by the atraumatic end 310 of the protective sheath 308 during delivery and/or retrieval of the biostimulator 100 from the patient. The atraumatic end 310 can have a braided or woven tubular construction. The atraumatic end 310 can therefore be advanced over the biostimulator 100 and may expand radially over the biostimulator 100 in the case where an outer dimension of the biostimulator 100 is greater than the inner diameter of the atraumatic end 310. Accordingly, the atraumatic end 310 can cover the biostimulator 100 to protect the biostimulator during advancement into the patient.

While delivering the biostimulator 100 to the target tissue, the elongated catheter 304 is likely to encounter several reaction forces. For example, when the biostimulator transport system 300 is "loaded" with a biostimulator, the system undergoes a large, mostly static compressive force to maintain intimate coupling of the biostimulator to the transport system. This compressive force resists de-coupling of the biostimulator from the transport system as it is tracked through the venous system into the patient heart. The transport system may be deflected via an integrated catheter pullwire (FIG. 5) to sweep the entire system through a deflection angle, e.g., 120 degrees, into a heart chamber from an inferior approach. Such deflection can be caused by pulling on the pullwire, and thus, a compressive force can be applied to the elongated catheter 304. The atraumatic end 310 may also track along tortuous vessels that will apply compressive forces to the distal catheter end 306. Similarly, when the biostimulator 100 is advanced toward the heart tissue to engage the tissue with the fixation element 106, the heart tissue will apply axial or lateral loads to the distal catheter end 306. Furthermore, rotation of the proximal handle portion 352 to screw the fixation element 106 into the heart tissue will be countered by resistance forces applied by the tissue to the fixation element 106. Therefore, to promote effective tracking and implantation of the biostimulator 100, the biostimulator transport system 300 can: have column strength and/or rigidity in an axial direction to promote trackability through tortuous vessels, be supple and flexible to allow deflection in bending such that tissue trauma is avoided either during tracking or engagement with the heart tissue, and transmit torque efficiently from the handle 302 to the docking cap 320 to drive the biostimulator 100 into the heart tissue.

Figure 5:
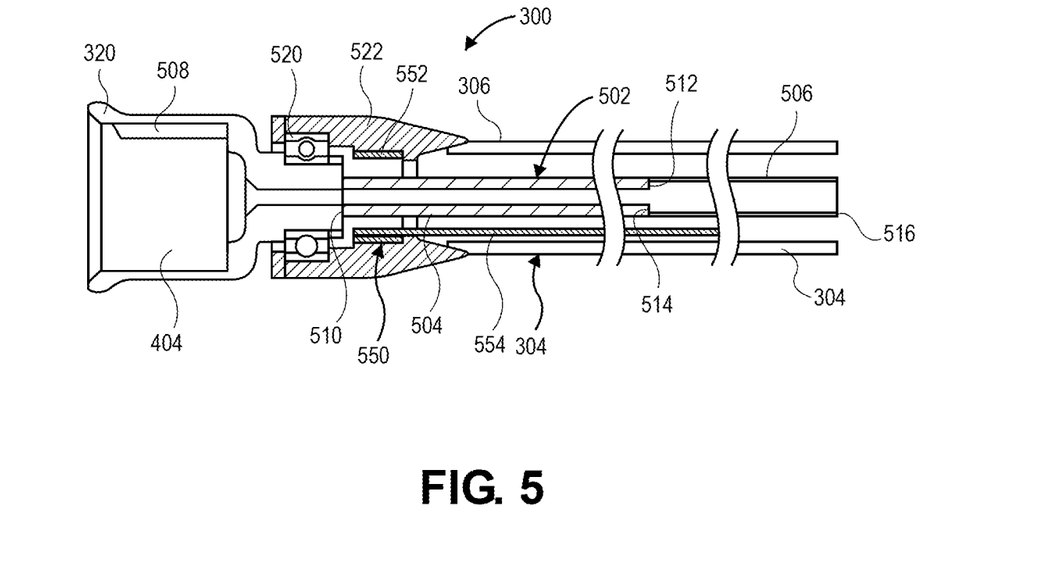
FIG. 5 is a cross-sectional view of a biostimulator transport system having a torque shaft assembly, in accordance with an embodiment.

Referring to FIG. 5, a cross-sectional view of a biostimulator transport system having a torque shaft assembly is shown in accordance with an embodiment. The elongated catheter 304 of the biostimulator delivery system can include a torque shaft assembly 502 to transmit torque from the handle 302 to the docking cap 320. More particularly, the torque shaft assembly 502 is torqueable and can be used to rotate the biostimulator 100 in a first direction, e.g., clockwise. Rotating the biostimulator in a first direction when the fixation element 106 is in contact with the heart tissue can cause the fixation element 106 to screw into the heart tissue and affix the biostimulator 100 to the heart tissue. By contrast, rotating the biostimulator 100 in a second direction opposite to the first direction when the fixation element 106 is affixed to the heart tissue can cause the fixation element 106 to unscrew from the heart tissue.

In an embodiment, the torque shaft assembly 502 includes a torque shaft 504, the docking cap 320, and a hypotube 506. The torque shaft assembly 502 components transmit torque from the handle 302 to the biostimulator 100, and can each function to facilitate that objective. As discussed above, the docking cap 320 can include a docking cavity 404 to receive the attachment feature 402 of the biostimulator 100 when the biostimulator is retracted against the docking cap 320 by the tethers 406. In an embodiment, the docking cap 320 further includes one or more key features 508 that interfere with a surface of the attachment feature 402 when torque is transmitted through the torque shaft 504 to the docking cap 320. Accordingly, the transmitted torque can be applied to the biostimulator 100 via the key feature 508 to cause the biostimulator 100 to rotate into, or out of, the target tissue.

The docking cap 320 can be mounted on the torque shaft 504. More particularly, the torque shaft 504 can have a distal shaft end 510 coupled to the docking cap 320, e.g., via a weld or adhesive joint. The torque shaft 504 can extend proximally from the docking cap 320 at the distal shaft end 510, which may be near, e.g., within 25 mm, of the distal catheter end 306, to a proximal shaft end 512 at a location intermediate between the distal shaft end 510 and the handle 302. The hypotube 506 can connect the proximal shaft end 512 to the handle 302, and thus, the proximal shaft end 512 may be coupled to the handle 302.

In an embodiment, the hypotube 506 is a solid, thin-walled tube having a distal tube end 514 joined to the proximal shaft end 512, and a proximal tube end 516 joined to the proximal handle portion 352 (not shown). The hypotube 506 can be cylindrical and extend over a proximal region of the elongated catheter 304, and thus, is primarily used in relatively straight segments of the patient anatomy. Accordingly, the hypotube 506 primarily requires axial stiffness and 1:1 torque transmission. As a result, the thin-walled tubular structure of the hypotube 506 can achieve the functional objectives of the system component. In an embodiment, the hypotube 506 has a length of at least 60 mm, and has a wall thickness of 0.005-0.010 inches. The hypotube 506 may be fabricated from a stiff, biocompatible material, such as full hard 304 stainless steel.

Interaction between the torque shaft assembly 502 and the handle 302 can be achieved in numerous manners. For example, the hypotube 506 can be directly connected to the proximal handle portion 352, which is rotatably coupled to the distal handle portion 350, as described above. For the sake of brevity, reference is made to previously filed patent applications that describe biostimulator transport systems 300 having a torque shaft 504 that interacts with a handle 302. The following publications include disclosures that are incorporated herein by reference: (1) U.S. application Ser. No. 15/783454, filed on Oct. 13, 2017, entitled "CATHETER-BASED SYSTEM FOR DELIVERY AND RETRIEVAL OF A LEADLESS PACEMAKER" and published as US2018/0303514A1 on Oct. 25, 2018; (2) U.S. application Ser. No. 15/783406, filed on Oct. 13, 2017, entitled "CATHETER-BASED SYSTEM FOR DELIVERY AND RETRIEVAL OF A LEADLESS PACEMAKER" and published as US2018/0303513A1 on Oct. 25, 2018; (3) U.S. application Ser. No. 15/942105, filed on Mar. 30, 2018, entitled "CATHETER-BASED DELIVERY SYSTEM FOR DELIVERING A LEADLESS PACEMAKER AND EMPLOYING A LOCKING HUB" and published as US2018/0280703A1 on Apr. 29, 2018; (4) U.S. application Ser. No. 15/783475, filed on Oct. 13, 2017, entitled "CATHETER-BASED SYSTEM FOR DELIVERY AND RETRIEVAL OF A LEADLESS PACEMAKER" and published as US2018/0104452A1 on Apr. 19, 2018; (5) U.S. application Ser. No. 15/783430, filed on Oct. 13, 2017, entitled "CATHETER-BASED SYSTEM FOR DELIVERY AND RETRIEVAL OF A LEADLESS PACEMAKER" and published as US2018/0104451A1 on Apr. 19, 2018; (6) U.S. application Ser. No. 15/783363, filed on Oct. 13, 2017, entitled "CATHETER-BASED SYSTEM FOR DELIVERY AND RETRIEVAL OF A LEADLESS PACEMAKER" and published as US2018/0104450A1 on Apr. 19, 2018; and (7) U.S. application Ser. No. 15/783298, filed on Oct. 13, 2017, entitled "CATHETER-BASED SYSTEM FOR DELIVERY AND RETRIEVAL OF A LEADLESS PACEMAKER" and published as US2018/0104449A1 on Apr. 19, 2018.

The biostimulator transport system 300 may include components that couple the torque shaft assembly 502 to the elongated catheter 304. In an embodiment, a bearing 520 supports the docking cap 320 and/or the torque shaft 504 relative to a docking hub 522. The bearing 520 can be a roller bearing 520, for example, and can provide smooth supported rotational motion between the docking cap 320 and the docking hub 522. The docking hub 522 can encase the distal end of the torque shaft 504. The docking hub 522 may be a collar component that mounts on and attaches to the distal catheter end 306 of the elongated catheter 304. Accordingly, when the torque shaft 504 is rotated, torque is transmitted to the docking cap 320 to allow it to spin freely relative to the docking hub 522, and related to an outer sheath of the elongated catheter 304 on which the docking hub 522 is mounted.

In an embodiment, the biostimulator transport system 300 is steerable. More particularly, by pivoting the deflection lever 303 toward a distal handle portion 350 of the handle 302, the operator can cause a pull ring assembly 550 to apply off-axis compression to the elongated catheter 304, resulting in lateral deflection of the distal catheter end 306. The pull ring assembly 550 can include a pull ring 552 attached to a distal end of a pull wire 554. The components may be attached by a weld or adhesive bond, for example. The pull ring 552 may, for example, be a metallic or polymeric annulus that fits within an interior of the docking hub 522. The pull ring 522 can interfere with a proximal portion of the interior, such that a proximal load applied to the pull ring 522 is transferred to the docking hub 522 and applies compression to the elongated catheter 304. In an embodiment, the pull wire 554 is a metallic or polymeric wire extending through the elongated catheter 304, e.g., between the outer sheath of the elongated catheter 304 and the torque shaft 502. The pull wire 554 can connect to the deflection lever 303, such that pivoting the lever applies an axial tension to the wire that pulls the pull ring 552 against the docking hub 522 to cause the biostimulator transport system 300 to deflect laterally and be steered to the target tissue.

Figure 6:
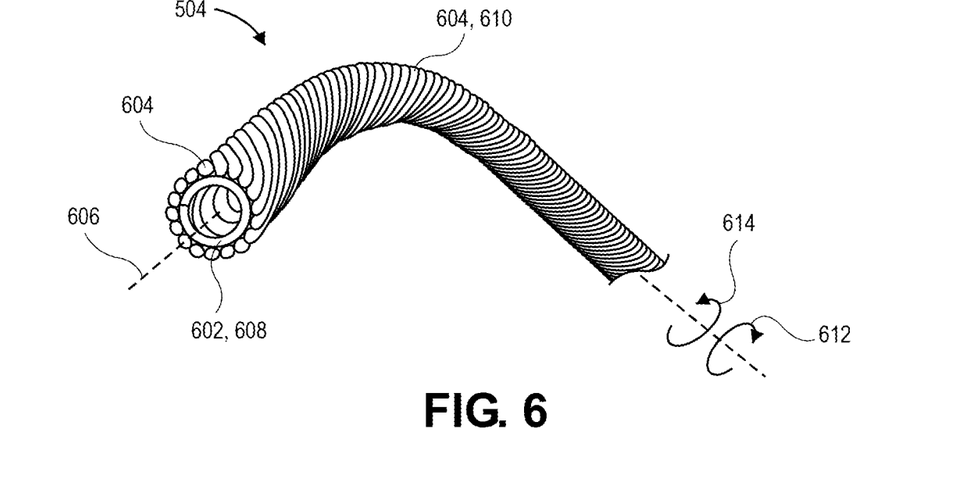
FIG. 6 is a pictorial view of a torque shaft, in accordance with an embodiment.

Referring to FIG. 6, a pictorial view of a torque shaft is shown in accordance with an embodiment. Whereas the hypotube 506 is primarily structured to maximize axial and torsional stiffness, the functional demands on the torque shaft 504 are different, and thus, the torque shaft 504 has a more complex structure. The torque shaft 504 is required to provide as close to 1:1 direct drive of the biostimulator as possible, however, the torque shaft 504 must also balance axial stiffness and suppleness to absorb compressive or bending loads during tracking. In an embodiment, a balance between torque transmission, axial stiffness, and suppleness is achieved using a swaged dual-layer construction. The torque shaft 504 can be fabricated from a same material as the hypotube 506, e.g., 304 stainless steel, or from another biocompatible material, such as nickel titanium. The dual-layer construction can improve torque transmission and can achieve the required column strength/rigidity while also being very flexible in bending (for deflection).

The torque shaft 504 having the swaged dual-layer construction includes an inner layer, e.g., an inner coil 602, within an outer layer, e.g., an outer cable 604. The inner coil 602 can be coaxially arranged with the outer cable 604 along a central axis 606. For example, the inner coil 602 can include one or more wire coils 608 wrapping around the central axis 606, and the outer cable 604 can include several outer strands 610 wrapping around the central axis 606. The wire coil(s) 608 can extend around the central axis 606 in a first helical direction 612, and the outer strands 610 can extend around the inner coil 602 in a second helical direction 614. In an embodiment, the first helical direction 612 is opposite to the second helical direction 614. For example, whereas the first helical direction 612 may be a right-handed rotational direction around the central axis 606, the second helical direction 614 may be a left-handed rotational direction around the central axis 606. The torque shaft 504 can be flexible due to the coiled structure of the wire coil(s) 608 and the outer strands 610, however, the dual-layer structure can support axial compression and torque transmission. To achieve such function, the inner and outer layers can compensate for and complement each other under axial and torsional loading. Under axial loading, the layers can stabilize each other to prevent buckling while still allowing some amount of give, e.g., when the biostimulator engages the target tissue. Under torsion, the layers can constrain diametric changes in each other to reduce wind up that may otherwise occur, e.g., in a single-layered torsional cable.

Figure 7:
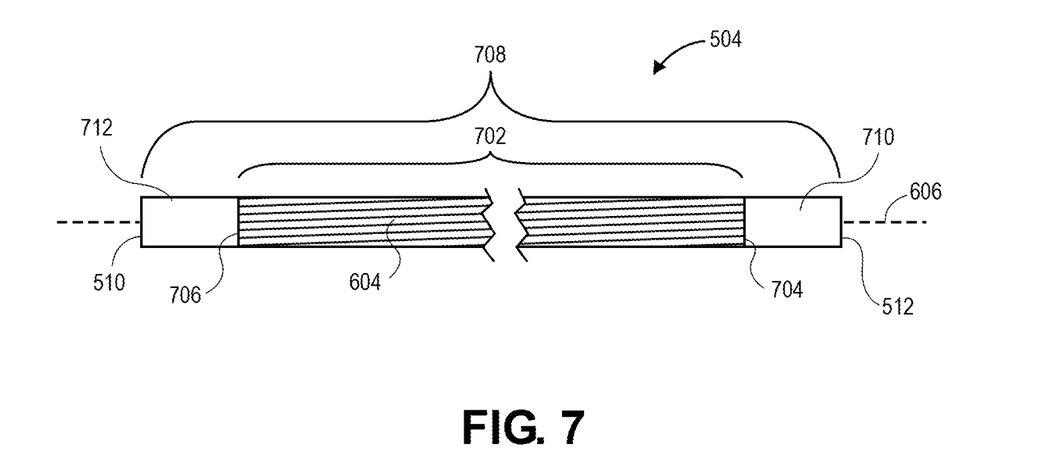
FIG. 7 is a side view of a torque shaft, in accordance with an embodiment.

Referring to FIG. 7, a side view of a torque shaft is shown in accordance with an embodiment. The inner coil 602 (hidden within the outer cable 604) can include a wire coil 608 extending about the central axis 606 over a coil length 702. More particularly, the inner coil 602 can extend through the outer cable 604 from a proximal coil end 704 to a distal coil end 706. Similarly, the outer cable 604 can extend helically around the central axis 606 from the proximal coil end 704 to the distal coil end 706.

The coil length 702 may be similar, but not necessarily identical, to a shaft length 708 of the torque shaft 504. More particularly, the shaft length 708 can be between the proximal shaft end 512 and the distal shaft end 510, and may be slightly longer than the coil length 702. The difference between these lengths can stem from one or more welds between the inner coil 602 and the outer strands 610 at the extremities of the torque shaft 504, e.g., at the ends of the tubular layers of the torque shaft 504. For example, a proximal weld 710 can join the inner coil 602 to the outer cable 604 at the proximal coil end 704 and/or a distal weld 712 can join the inner coil 602 to the outer cable 604 at the distal coil end 706. Accordingly, the shaft length 708 may be an entire length of the torque shaft 504, including the weld zones, and the coil length 702 may be a portion of the shaft length 708 over which the inner coil 602 and the outer cable 604 are not directly joined by a bond, but may nevertheless be indirectly joined, via swaging, as described below.

In an embodiment, the welds at the extremities of the torque shaft 504 extend circumferentially around the torque shaft 504. More particularly, the proximal weld 710 and/or the distal weld 712 can fuse the inner layer and the outer layer around an entire circumference of the torque shaft 504 about the central axis 606. The circumferential welds can form collar sections, e.g., tubular sections, having lengths of 0.02-0.25 inches in length, e.g., 0.04 inches long. The collar sections may be entirely fused, e.g., there may be no gaps or holes visible in the collar sections under magnification. The welds can be formed using known welding processes, e.g., laser welding. The welded collars can provide attachment points to join the torque shaft 502 to the docking cap 320 and/or the hypotube 506.

Figure 8:
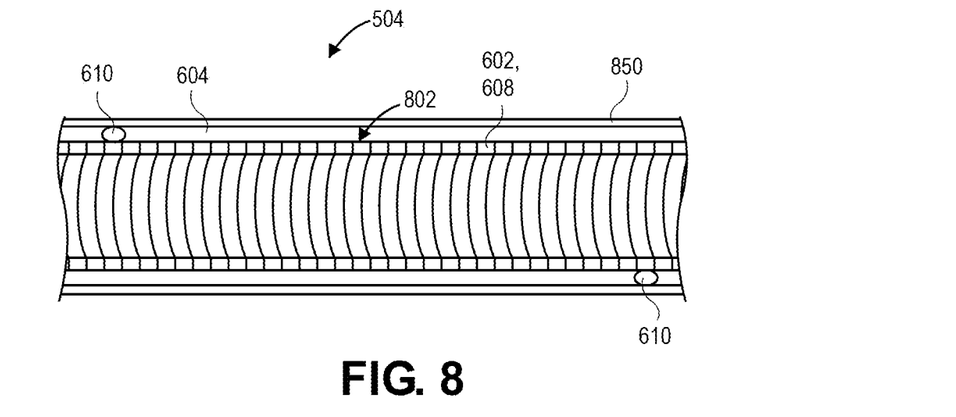
FIG. 8 is a cross-sectional side view of a torque shaft, in accordance with an embodiment.

Referring to FIG. 8, a cross-sectional side view of a torque shaft is shown in accordance with an embodiment. The inner coil 602 can include a single wire coil 608, e.g., a single wound wire, wound in the first helical direction 612. For example, the single wire coil 608 can be right hand wound. In an embodiment, the wire coil 608 has a quadrilateral cross-sectional profile. For example, the wire coil 608 can include a rectangular wire having a rectangular cross-sectional profile including height and width dimensions in a range of 0.1 to 0.5 mm, e.g., 0.15 mm by 0.3 mm. The rectangular cross-sectional profile allows the individual turns of the wire coil 608 to stack on each other, which can provide a stable columnar structure. For example, the wire coil 608 can have several turns that are in contact with each other such that the inner coil 602 is a stacked coil tube 802. The stacked coil tube 802 may have no gaps between the turns, as shown in FIG. 8, in an undeformed state. Accordingly, the inner coil 602 can have high columnar strength, yet can be flexible in bending, e.g., when a lateral load is applied to the stacked coil tube 802 the coil can bend and gaps can occur between the turns in the deformed state.

In an embodiment, the outer cable 604 is swaged, either before or after loading the outer cable onto the inner coil 602. For example, the outer cable 604 can be swaged directly onto the inner coil 602. Alternatively, the outer cable 604 can be swaged and then loaded onto the inner coil 602. Swaging refers to a process in which one or more of the outer cable 604 or the inner coil 602 are radially compressed between surfaces, e.g., a mandrel and an outer die, to cause the compressed layer(s) to be cold-worked. The assembled layers can therefore be tightly-formed relative to each other. As described below, the cold-working can cause a cold-forming reduction in diameter of the outer cable 604 around the inner coil 602 to form a friction fit between the outer strands 610 and the wire coil 608. Alternatively, the outer cable 604 can be cold-worked onto a mandrel, and then the post-swaged outer cable 604 can be loaded onto the inner coil 602 to form a slip fit. In an embodiment, the outer cable 604 is swaged, e.g., onto the inner coil 602, over an entirety of the coil length 702 from the distal coil end 706 to the proximal coil end 704. Alternatively, the outer cable 604 may be swaged over only a portion of the coil length 702. For example, a stitch-swaging process may be used to swage the layers over several segments intermittently spaced between the distal coil end 706 and the proximal coil end 704.

Figure 9A:
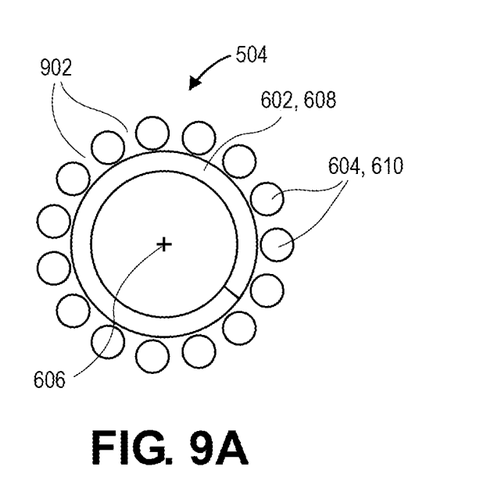
FIGS. 9A-9B are cross-sectional end views of a torque shaft in pre-swaged and post-swaged states, in accordance with an embodiment.

Referring to FIGS. 9A, a cross-sectional end view of a torque shaft 504 in a pre-swaged state is shown in accordance with an embodiment. As compared to the single-stranded structure of the wire coil 608, the outer cable 604 includes several outer strands 610 that are wound in a predominantly axial direction around the central axis 606. For example, the outer cable 604 may include 15 outer strands 610 wound in the second helical direction 614, e.g., the strands can be left hand wound. The strands 610 can overlay the wire coil 608, and an angle formed between a helical axis of the wire coil 608 and a helical axis of each of the strands may be orthogonal, or nearly orthogonal. More particularly, a direction of the helical axis of the wire coil 608 can be predominantly circumferential and a direction of the helical axis of the outer strands 610 can be predominantly axial.

Figure 9B:
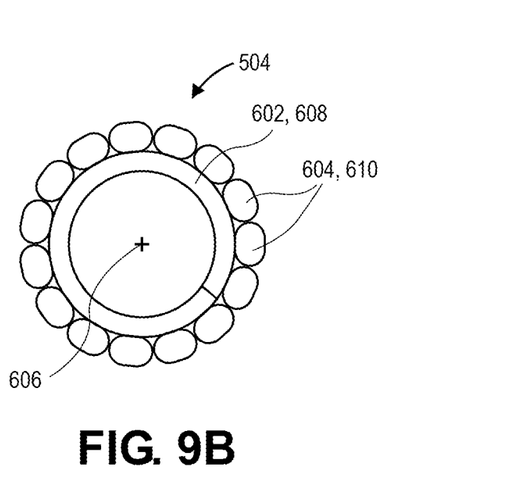

The outer strands 610 may have a pre-swaged cross-sectional profile (FIG. 9A) and a post-swaged cross-sectional profile (FIG. 9B). The pre-swaged and post-swaged cross-sectional profiles can differ because the swaging process can deform the outer strands 610 to reduce and conform the outer cable 604 to the inner coil 602. In an embodiment, the pre-swaged cross-sectional profile is round. For example, the outer strands 610 can be formed from round wire stock, such as 0.2 mm diameter round wire, that is formed into a helically stranded tube prior to swaging. In the pre-swaged state, one or more circumferential gaps 902 may be located between adjacent outer strands 610. Furthermore, the pre-swaged outer cable may fit over the pre-swaged inner coil 602 in a sliding fit, e.g., a radial gap can be present between the layers at locations along the torque shaft 504.

Referring to FIG. 9B, a cross-sectional end view of a torque shaft in a post-swaged state is shown in accordance with an embodiment. The post-swaged cross-sectional profile of the outer strands 610 and/or the wire coil 608 can be non-round. For example, each of the outer strands 610 may have, after swaging, an oblong or elliptical outer profile. The elliptical profile can result from the squeezing of the round profile into a post-swaged state. In the post-swaged state, the outer strands 610 can be in contact with each other such that the outer cable 604 is tubular. More particularly, there may be no gaps greater than 0.01 inches between the outer strands 610 over the length of the swaged regions. Accordingly, the pre-swaged helically-stranded tube having openings through the tube wall can become the post-swaged helically-stranded tube having a closed wall.

The illustrated cross-sectional profiles of the outer cable 604 and the inner coil 602 in the pre-swaged and post-swaged states are provided by way of example, and other cross-sectional profiles and profile combinations are within the scope of this description. For example, the single wire coil 608 may have a round, e.g., circular or elliptical, cross-sectional profile in the pre-swaged and/or post-swaged state. By contrast, the outer strands 610 of the outer cable 604 may have rectangular cross-sectional profiles in the pre-swaged and/or post-swaged state. Furthermore, the cross-sectional profiles of the wire coil 608 and the outer strands 610 may be the same, and the profiles may be round or non-round, e.g., elliptical, polygonal, etc. Accordingly, the respective profiles of the inner and outer layers may be varied within the scope of this description, and are not limited by the embodiments provided.

Figure 10:
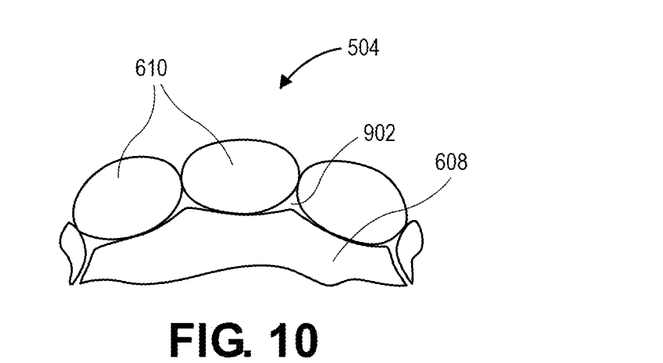
FIG. 10 is a detail view of a torque shaft in a post-swaged state in which outer strands form a friction fit with a wire coil, in accordance with an embodiment.

Referring to FIG. 10, a detail view of a torque shaft in a post-swaged state in which outer strands form a friction fit with a wire coil is shown in accordance with an embodiment. The swaged layers of the torque shaft 504 can form a friction fit that resists relative motion between the outer cable 604 and the inner coil 602. The friction fit can be caused in part by squeezing the coil and strand materials together. For example, the wire coil 608 can bulge into the remaining circumferential gaps 902 of the outer strands 610 and/or the outer strands 610 can embed in a radially outward surface of the inner coil 602. The friction fit can support axial loading, e.g., the torque shaft 504 may resist at least 30 lbf of axial compression without separating the inner coil 602 from the outer cable 604. Furthermore, the friction fit can support torque transmission, e.g., the swaged regions have layers that resist movement of each other and therefore reduce a likelihood of wind up in the torque shaft structure. Accordingly, the coaxial swaged torque shaft 504 provides good trackability and direct correlation between input rotation at the proximal shaft end 512 and outer rotation at the distal shaft end 510.

In an embodiment, one or more of the layers can be swaged to form a slip fit between the outer strands 604 and the wire coil 608. For example, the outer cable 604 may be swaged onto a mandrel having an outer diameter that is the same or slightly larger than an outer dimension of the inner coil 602. Similarly, the wire coil 608 may be swaged onto a respective mandrel. The layer(s) can be removed from their respective mandrels, and the outer cable 604 can then be slipped onto the inner coil 602 in the post-swaged state such that the outer strands 604 form a slip fit with the wire coil 608. The inner and outer layers can be attached to each other via weld(s) 710, 712 to form the torque shaft 504 having a slip fit configuration. It will be appreciated that the slip fit configuration can have sufficient interference between the layers to reduce a likelihood of wind up during torque transmission, and thus, can improve torque transmission through the torque shaft 504. More particularly, the slip fit can support axial compression and torque transmission, as described above.

Figure 11:
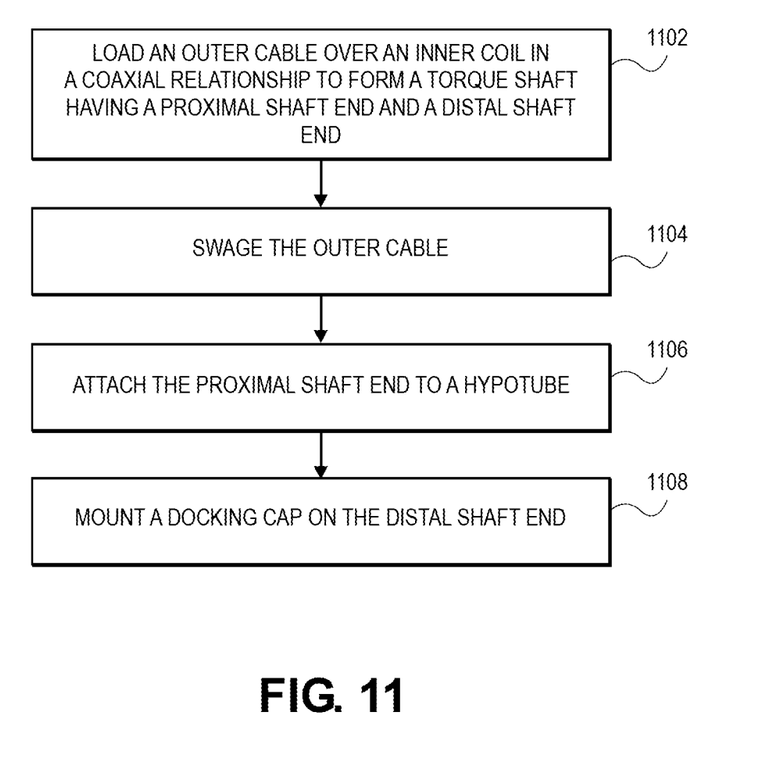
FIG. 11 is a flowchart of a method of manufacturing a torque shaft assembly, in accordance with an embodiment.

Referring to FIG. 11, a flowchart of a method of manufacturing a torque shaft assembly is shown in accordance with an embodiment. The torque shaft assembly 502 can be fabricated in a variety of manners, and one such process is described below. At operation 1102, the outer cable 604 is loaded over the inner coil 602. The assembled layers can be in a coaxial relationship. Optionally, one or more welds can be formed at the extremities of the inner and outer layers to form the torque shaft 504. For example, a laser welding process can form the distal weld 712 and the proximal weld 710. The welds may be circumferentially continuous to fuse the torque shaft layers around the entire shaft perimeter. The torque shaft 504 can therefore include the distal shaft end 510 and the proximal shaft end 512.

At operation 1104, the outer cable 604 is swaged. Swaging of the outer cable 604 can occur before or after operation 1102. For example, when the outer cable 604 is swaged and then loaded onto the inner coil 602 to form a slip fit, operation 1104 can precede operation 1102. By contrast, when the outer cable 604 is swaged directly onto the inner coil 602 to form a friction fit, operation 1102 can precede operation 1104.

In an embodiment, operation 1104 precedes 1102. The outer cable 604 and/or the inner coil 602 can be placed on respective mandrels. The layer(s) may be swaged over an entirety of the shaft length 708 or only a portion of the shaft length 708. For example, the outer cable 604 and the inner coil 602 may be swaged to respective diameters such that, when the outer cable 604 is loaded onto the inner coil 602, the layers form a slip fit.

In an embodiment, operation 1102 precedes 1104. As a preliminary operation, the inner coil 602 may be placed on a mandrel having an outer diameter that is the same size as a desired inner diameter of the torque shaft 504. The outer cable 604 can be loaded over the inner coil 602. Optionally, the outer cable 604 can be pre-swaged. More particularly, the helically-stranded tubular structure of the outer cable 604 can be swaged to transition the cable from the pre-swaged state (FIG. 9A) to the post-swaged state (FIG. 9B). In either case, the outer cable 604 can be placed on the inner coil 602, and the dual-layer pre-assembly can be supported on the mandrel. The outer cable 604 may then be swaged directly onto the inner coil 602 to form a friction fit between the layers.

In the swaging processes described above, the swaged component (the outer cable 604 and/or the inner coil 602) can be swaged to varying degrees at discrete locations between the proximal shaft end 512 and the distal shaft end 510. In an embodiment, the outer cable 604 is swaged to a greater degree, e.g., to a smaller outer diameter, at a location near the proximal shaft end 512 than at a location near the distal shaft end 510. This variation in swaging over the length of the torque shaft 504 can include swaging more near the proximal end near the handle 302. The swaging at the proximal end can form a stiffness that more closely matches the hypotube stiffness at that location. The increased stiffness can facilitate axial stiffness and torque transmission. By contrast, swaging less near the distal end can provide a more flexible region at that location, which may be better for tracking through tortuous vessels and absorbing impacts with the target tissue.

At operation 1106, the proximal shaft end 512 may be attached to the hypotube 506. A bonding process, such as welding, may be used to attach the torque shaft 504 to the hypotube 506. Similarly, at operation 1108, the distal shaft end 510 may be attached to the docking cap 320. A bonding process, such as welding, may be used to attach the torque shaft 504 to the docking cap 320. Accordingly, a torque shaft assembly 502 can be provided for integration in the biostimulator transport system 300. The torque shaft assembly 502 can improve torque transmission from the handle 302 to the docking cap 320 by providing a 1:1 direct drive transmission shaft, and the torque shaft 504 can be trackable and supple.

Figure 12:
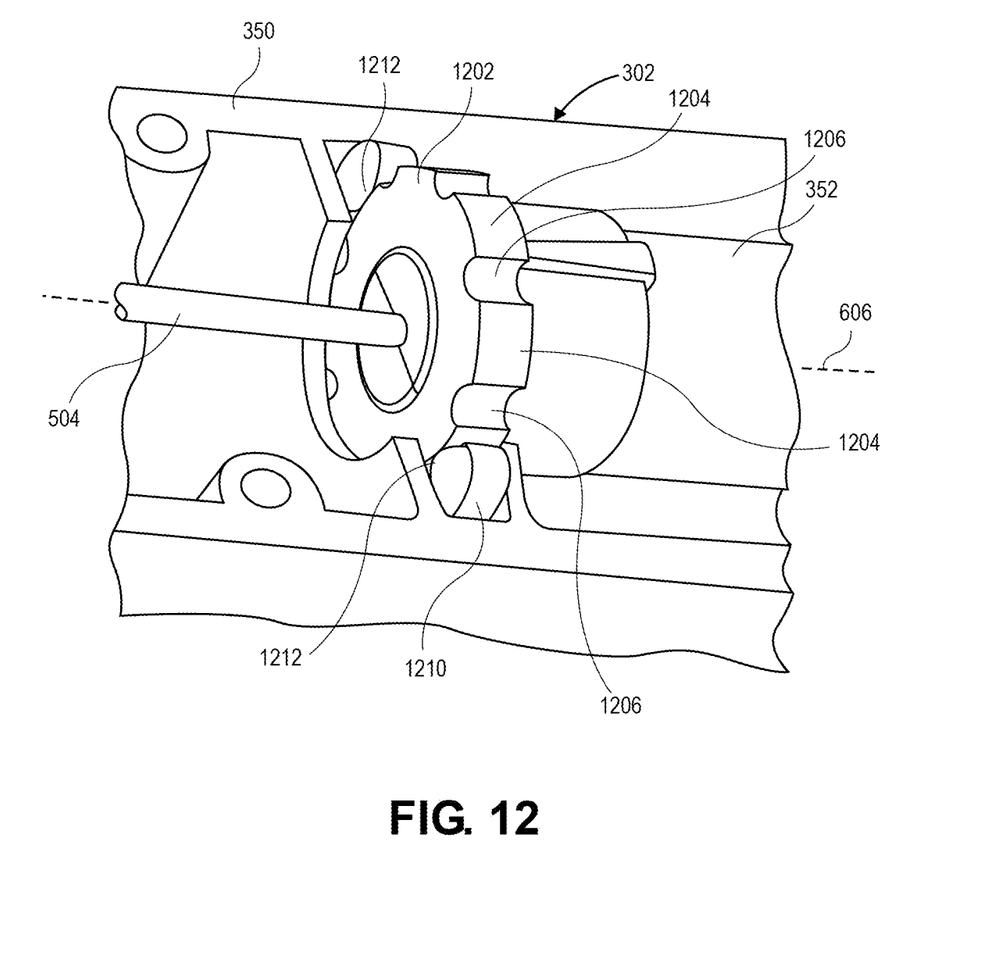
FIG. 12 is a perspective view of a handle having a rotation feedback mechanism, in accordance with an embodiment.

Referring to FIG. 12, a perspective view of a handle having a rotation feedback mechanism is shown in accordance with an embodiment. As described above, the swaged coaxial torque shaft 504 improves torque transmission and can reduce wind up in the shaft, which translates to 1:1 (or near 1:1) correspondence between input rotations at the handle 302 and output rotations at the docking cap 320. The improved correspondence between input and output rotation can allow for improved granularity of device control by an operator. More particularly, the operator can rotate the input control of the handle 302 over a smaller angle and have increased confidence that the same small angle will be reproduced at the output of the docking cap 320, rather than being absorbed in torsion of the shaft. The input control can include a feedback mechanism to indicate to the operator that a particular amount of rotation has been input to the torque shaft. A particular embodiment of the input control is described below.

In an embodiment, the handle 302 includes the distal handle portion 350 and the proximal handle portion 352. The proximal handle portion 352 can be rotated about the central axis 606 to rotate relative to the distal handle portion 350. Furthermore, rotation of the torque shaft 504 can be fixed to rotation of the proximal handle portion 352. More particularly, when the operator rotates the proximal handle portion 352 relative to the distal handle portion 350, the torque shaft 504 can also rotate relative to the distal handle portion 350. The torque shaft 504 can be coupled to the proximal handle portion 352. For example, a distal end of the proximal handle portion 352 can be mounted on the proximal shaft end 512. Accordingly, rotation of the proximal handle portion 352 is an input rotation to the proximal shaft end 512.

In an embodiment, the handle 302 includes a detent ring 1202. The detent ring provides feedback to the operator that indicates an amount of input rotation applied to the torque shaft 504. The detent ring 1202 can be mounted on a distal end of the proximal handle portion 352, such that, as the proximal handle portion 352 rotates, the detest ring 1202 rotates. In an embodiment, the detent ring 1202 has a disc-shaped head having a circumferential outer surface 1204. The circumferential outer surface 1204 includes one or more detents 1206, which are recessed in the circumferential outer surface 1204. More particularly, a radial distance between the central axis 606 and the detents 1206 is less than a radial distance between the central axis 606 and the outermost surfaces of the circumferential outer surface 1204. The detents 1206 cause the circumferential outer surface 1204 to be bumpy, and more particularly, the detents 1206 cause intermittent recesses around the circumference of the detent ring 1202. For example, there may be 8 detents evenly spaced around the circumferential outer surface 1204.

The detent ring 1202, which is mounted on the proximal handle portion 352, can interface with a snick clip 1210. In an embodiment, the snick clip 1210 is fixed to the distal handle portion 350. For example, the snick clip 1210 can be mounted within a slot formed in the wall of the distal handle portion 350, and optionally, may be bonded to the distal handle portion 350. The snick clip 1210 can have an inner arc that receives the detent ring 1202. The detent ring 1202 can be aligned to the inner arc, and thus, can rotate about the central axis 606 within the inner arc. In an embodiment, the snick clip 1210 includes one or more protrusions 1212 extending radially inward from the inner arc. For example, the snick clip 1210 can have a pair of protrusions diametrically opposed to each other about the circumferential outer surface 1204 of the detent ring 1202. The protrusions 1212 can extend into contact with the detent ring 1202. For example, as the detent ring 1202 rotates within the snick clip 1210, the protrusions can ride over the bumpy surface of the circumferential outer surface 1204. More particularly, the protrusions can ride over the outermost portions of the surface 1204, and ride over the detents 1206. As the protrusions 1206 transition into the detents 1206, a tactile click can be felt in the handle 302. This click is the result of the protrusions 1212 snapping into the detents 1204. Accordingly, the engagement of the detent ring 1202 and snick clip 1210 can provide tactile feedback to a user indicating that a particular input rotation has been transmitted to the torque shaft 504.

In an embodiment, the detent ring 1202 includes at least 4, e.g., 8, evenly spaced detents 1204. Thus, each click of the snick clip 1210 corresponds to at least 90 degrees, e.g., 45 degrees, of rotation input to the torque shaft 504. That is, in the case of 8 detents, as the protrusions 1212 exit a first detent, ride over the outermost surface of the detent ring 1202, and click into place within a second adjacent detent, the input rotation will have been 45 degrees.

It will be appreciated that 1:1 correspondence between the input to the torque shaft 504 and the output of the torque shaft 504 allows for more detents 1204 to be included on the detent ring 1202, and thus, improves the granularity of feedback to the operator. For example, when torque transmission is worse than 1:1, e.g., when 90 degrees of input is required to overcome wind up and cause rotation at the output, the detent spacing must be at least 90 degrees or else the operator will receive a tactile click that indicates a degree of rotation at the input end that does not correspond to an actual rotation at the output end. By contrast, as torque transmission approaches 1:1, there is less wind up and the tactile clicks associated with closely spaced detents can actually correspond to an output rotation. For example, the biostimulator transport system 300 including the swaged coaxial torque shaft 504 can have 8 detents, and each time the operator receives a click when rotating the proximal handle portion 352 relative to the distal handle portion 350, a 45 degree output can result at the docking cap 320.

Referring again to FIG. 8, optionally, an outer sleeve 850 may be used in addition to or instead of swaging the outer cable 604. Such optional feature may be omitted, however, as is clear from the illustrations of FIGS. 9A-9B, which do not show the outer sleeve 850. The outer sleeve 850 can reduce a likelihood that the outer strands 610 of the outer cable 604 will expand during use. More particularly, the sleeve 850 can be a thin-walled tubular component that contains the inner coil 602 and the outer cable 604 of the torque shaft assembly 502. The sleeve 850 can be fabricated from a material that facilitate a thin wall, such as polyethylene terephthalate or polyimide. The sleeve 850 can extend over at least a portion of, e.g., an entire length or less than an entire length of, the outer cable 604. For example, the outer sleeve 850 can extend from a proximal sleeve end to a distal sleeve end, and be attached at the sleeve ends to the outer cable 604.

The tubular sleeve 850 can have an inner diameter that matches, e.g., equals, the outer diameter of the outer cable 604. More particularly, the sleeve 850 can form a sliding or friction fit with the outer cable 604. In an embodiment, the sleeve is formed from a heat shrinkable material, e.g., polyolefin. Accordingly, a press fit between the sleeve 850 and the outer cable 604 can be thermally induced. The close fit between the sleeve 850 and the outer cable 604 can limit expansion of the outer strands 610. For example, when torque is applied to the torque shaft 504, the outer strands 610 may be urged to unwind and expand in diameter, as previously discussed. The sleeve 850, however, may have a solid or semi-solid wall that does not expand, and thus, the outer strands 610 can expand against an interior surface of the sleeve 850. More particularly, the interior surface of the sleeve 850 can constrain the outer strands 610. The outer cable 604 may therefore remain at an initial diameter. The constrained strands can remain in contact with the inner coil 602, and thus, torque transmission can be efficiently transferred as described above. Accordingly, the sleeve 850 can facilitate torque transmission through the torque shaft 504.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A torque shaft assembly, comprising:
   an inner coil including a wire coil extending about a central axis along an inner helical axis in a first helical direction over a coil length between a proximal coil end and a distal coil end; and
   an outer cable including a plurality of outer strands extending helically around the inner coil along respective outer helical axes in a second helical direction from the proximal coil end to the distal coil end, wherein the torque shaft assembly includes welds between the outer cable and the inner coil at the proximal coil end and the distal coil end, wherein the outer cable is swaged onto the inner coil over a plurality of swaged sections between the welds at the proximal coil end and the distal coil end such that an outer surface of the outer cable is flattened and the wire coil bulges into circumferential gaps between the plurality of outer strands to form an annular wall around a central lumen, and wherein stiffnesses of the plurality of swaged sections decrease in a distal direction between the welds at the proximal coil end and the distal coil end.

2. The torque shaft assembly of claim 1, wherein the plurality of outer strands form one or more of a friction fit or a slip fit with the wire coil.

3. The torque shaft assembly of claim 1, wherein the outer cable is swaged over an entirety of the coil length.

4. The torque shaft assembly of claim 1, wherein the outer cable is swaged over only a portion of the coil length.

5. The torque shaft assembly of claim 1, wherein the plurality of outer strands have a pre-swaged cross-sectional profile that is different than a post-swaged cross-sectional profile.

6. The torque shaft assembly of claim 1, wherein one or more of the wire coil or the plurality of outer strands have a rectangular cross-sectional profile.

7. The torque shaft assembly of claim 1, wherein the first helical direction is opposite to the second helical direction.

8. The torque shaft assembly of claim 1, wherein the plurality of outer strands are in contact with each other such that the outer cable is tubular.

9. The torque shaft assembly of claim 1, wherein the wire coil has a plurality of turns in contact with each other such that the inner coil is a stacked coil tube.

10. The torque shaft assembly of claim 1, wherein an outer diameter of the outer surface of the outer cable increases in the distal direction between the proximal coil end and the distal coil end.

11. A biostimulator transport system, comprising:
    a handle;
    a docking cap having a docking cavity to receive an attachment feature of a biostimulator; and
    a torque shaft having a proximal shaft end coupled to the handle and a distal shaft end coupled to the docking cap, wherein the torque shaft includes an inner coil including a wire coil extending about a central axis along an inner helical axis in a first helical direction, and an outer cable including a plurality of outer strands extending helically around the inner coil along respective outer helical axes in a second helical direction, wherein the outer helical axes are orthogonal to the inner helical axis, wherein the torque shaft includes welds between the outer cable and the inner coil at the proximal shaft end and the distal shaft end, wherein the outer cable is swaged onto the inner coil over a plurality of swaged sections between the welds at the proximal shaft end and the distal shaft end such that an outer surface of the outer cable is flattened and the wire coil bulges into circumferential gaps between the plurality of outer strands to form an annular wall around a central lumen, and wherein stiffnesses of the plurality of swaged sections decrease in a distal direction between the welds at the proximal coil end and the distal coil end.

12. The biostimulator transport system of claim 11 further comprising a hypotube connecting the proximal shaft end to the handle.

13. The biostimulator transport system of claim 12, wherein the handle includes a proximal handle portion that is rotationally moveable relative to a distal handle portion, and wherein the proximal handle portion is coupled to the hypotube.

14. The biostimulator transport system of claim 13, wherein the outer cable is swaged over an entirety of a coil length of the inner coil such that the plurality of outer strands form one or more of a friction fit or a slip fit with the wire coil.

15. The biostimulator transport system of claim 13, wherein the first helical direction is opposite to the second helical direction.

16. The biostimulator transport system of claim 13, wherein the plurality of outer strands are in contact with each other such that the outer cable is tubular.

17. The biostimulator transport system of claim 13, wherein the wire coil has a plurality of turns in contact with each other such that the inner coil is a stacked coil tube.

18. A method of manufacturing a torque shaft assembly, comprising:
loading an outer cable over an inner coil to form a torque shaft having a proximal shaft end and a distal shaft end, wherein the inner coil includes a wire coil extending about a central axis along an inner helical axis in a first helical direction, wherein the outer cable includes a plurality of outer strands extending helically around the inner coil along respective outer helical axes in a second helical direction, and wherein the outer helical axes are orthogonal to the inner helical axis;
welding the outer cable to the inner coil at the proximal shaft end and the distal shaft end; and
swaging the outer cable onto the inner coil over a plurality of swaged sections between the welds at the proximal shaft end and the distal shaft end such that an outer surface of the outer cable is flattened and the wire coil bulges into circumferential gaps between the plurality of outer strands to form an annular wall around a central lumen, and wherein stiffnesses of the plurality of swaged sections decrease in a distal direction between the welds at the proximal coil end and the distal coil end.

19. The method of claim 18 further comprising attaching the proximal shaft end to a hypotube.

20. The method of claim 19 further comprising mounting a docking cap on the distal shaft end, wherein the docking cap has a docking cavity to receive an attachment feature of a biostimulator.

21. A torque shaft assembly, comprising:
an inner coil including a wire coil extending about a central axis along an inner helical axis in a first helical direction over a coil length between a proximal coil end and a distal coil end;
an outer cable including a plurality of outer strands extending helically around the inner coil in a second helical direction along respective outer helical axes from the proximal coil end to the distal coil end, wherein the torque shaft assembly includes welds between the outer cable and the inner coil at the proximal coil end and the distal coil end, wherein the outer cable is swaged onto the inner coil over a plurality of swaged sections between the welds at the proximal coil end and the distal coil end such that an outer surface of the outer cable is flattened and the wire coil bulges into circumferential gaps between the plurality of outer strands to form an annular wall around a central lumen, and wherein stiffnesses of the plurality of swaged sections decrease in a distal direction between the proximal coil end and the distal coil end; and
an outer sleeve containing the inner coil and the outer cable.

22. The torque shaft assembly of claim 21, wherein the outer sleeve is a tubular component having an inner diameter equal to an outer diameter of the outer cable.

23. The torque shaft assembly of claim 22, wherein the outer sleeve is attached to the outer cable at a proximal sleeve end and a distal sleeve end.

24. The torque shaft assembly of claim 21, wherein the plurality of outer strands have a pre-swaged cross-sectional profile that is different than a post-swaged cross-sectional profile.

25. The torque shaft assembly of claim 21, wherein one or more of the wire coil or the plurality of outer strands have a rectangular cross-sectional profile.

26. The torque shaft assembly of claim 21, wherein the first helical direction is opposite to the second helical direction.

* * * * *